United States Patent [19]

Moore

[11] Patent Number: 5,674,904

[45] Date of Patent: Oct. 7, 1997

[54] METHOD FOR THE TREATMENT OF CYANIDE POISONING

[76] Inventor: Steven Jerome Moore, 9 Sonoma Rd., Cortlandt Manor, N.Y. 10566

[21] Appl. No.: 581,803

[22] Filed: Jan. 2, 1996

[51] Int. Cl.$^6$ ............................ A61K 31/70; A61K 31/19
[52] U.S. Cl. ............................ 514/574; 514/52; 514/823
[58] Field of Search ........................... 514/52, 574, 823

[56] References Cited

PUBLICATIONS

CA 104:103873, Moore et al., 1986.
CA 80:91833, Alves de Souza et al., 1971.

*Primary Examiner*—Kimberly Jordan

[57] ABSTRACT

2-oxopropanedioic acid is an extremely effective antidote for cyanide poisoning even at low doses.

4 Claims, No Drawings

METHOD FOR THE TREATMENT OF CYANIDE POISONING

BACKGROUND OF INVENTION

1. Field of Invention

The field of the present invention generally relates to a method for treating cyanide poisoning. More specifically, it relates to the use of 2-oxopropanedioic acid in cyanide-intoxicated mammals.

2. Brief Description of the Prior Art

Numerous persons are inflicted with cyanide poisoning each year. Poisoning may occur owing to occupational exposure. Cyanide is employed in the hardening of steel, fumigation, and in chemical manufacturing, e.g. in polymerization reactions. A significant amount of cyanide salt is also used in the extraction of gold and silver from ore. Such extraction procedures not infrequently leave mounds of toxic cyanide waste which are typically buried to prevent mass exposure.

Hydrogen cyanide exposure may occur when certain synthetic polymers such as polyamides (e.g. nylon) and polyacrylonitriles (e.g. Orlon®), as well as some natural products, such as wool, are burned. Many fire deaths are believed to be related to the inhalation of smoke contaminated with hydrogen cyanide gas.

Over the past century several antidotes to cyanide poisoning have been proposed in the art. These antidotes generally can be broken down into three broad classifications—those compounds that hasten the metabolism of cyanide, those compounds that alter hemoglobin such that it can bind cyanide, and those compounds which bind cyanide by themselves.

Of the compounds that hasten the metabolism of cyanide, sodium thiosulfate is perhaps best known. Cyanide is primarily metabolized in the body to the less toxic substance thiocyanate by a enzyme known as rhodanese. The limiting factor in rhodanese conversion of cyanide to thiocyanate is the amount of thiol substrate available to the enzyme. Sodium thiosulfate acts as an exogenous source of such substrate thus speeding up the metabolism of cyanide.

A number of cyanide antidotes work by oxidizing hemoglobin to methemoglobin. Methemoglobin tenaciously binds cyanide radicals. One of the earliest methemoglobin formers used as a cyanide antidote was methylene blue, a weak methemoglobin-former which is rarely used today. The methemoglobin-formers of choice today include amyl nitrite, an antidote administered by inhalation, and sodium nitrite, an antidote give intravenously. Methemoglobin-bound cyanide reduces the amount of free cyanide available to react at the cellular level.

Several compounds that bind cyanide by themselves have also been proposed as cyanide antidotes. One of these cobalt EDTA is used extensively in Europe. Others such as hydroxocobalamin and a-keto glutaric acid have been widely promoted in the United States. Studies suggest that compounds which bind cyanide by themselves, rather than those which form methemoglobin, may be the most appropriate antidotes to use in smoke inhalation victims also suffering from concomitant hypoxia.

Each of the cyanide antidotes available today suffers from a disadvantage. Sodium thiosulfate, while being quite efficacious in treating non-acute cases of cyanide poisoning, works too slowly to be useful in persons who have been exposed to lethal doses of cyanide. Sodium nitrite and amyl nitrite, while quite effective in treating even acute cases of cyanide poisoning, are generally not useful in treating persons who are concomitantly suffering from hypoxia secondary to another toxin, such as carbon monoxide. Cobalt EDTA, while being the cyanide antidote of choice in many European countries, suffers from it propensity to cause ventricular arrhythmias in some people. Hydroxocobalamin, pyruvic acid and a-ketoglutarate, while demonstrating effectiveness in treating both acute and non-acute cyanide poisoning, may be required to be given in bolus doses which are considerably larger than desired.

SUMMARY OF THE INVENTION

It has been discovered that 2-oxopropanedioic acid is an extremely effective antidote for cyanide poisoning even at low doses. It has further been discovered that 2-oxopropanedioic acid, as well as other direct cyanide binding agents of cyanide, when admixed with aqueous solution of cyanide salt produces a considerably less toxic substance than the cyanide salt itself.

In a preferred embodiment of the present invention, a non-toxic, pharmaceutically effective dose of 2-oxopropanedioic acid is administered prior to, or after, exposure to cyanide by a therapeutically effective route of administration. In a particularly preferred embodiment, 2-oxopropanedioic acid is admixed with one or more second cyanide antagonists of lower toxicity, but less affinity for cyanide, to reduce the amount of such second antagonist needed for the treatment of cyanide poisoning.

In one embodiment of the present invention, waste cyanide from e.g. a metallurgical extraction of gold is admixed in an aqueous solution with a direct-binding cyanide antidote, including, but not limited to 2-oxopropanedioic acid, pyruvic acid, and a-ketoglutaric acid. The solution is dried and the less toxic substance produced thereby becomes the waste.

In another embodiment of the present invention, there is disclosed a method for reducing the toxicity of cyanide waste comprising admixing said cyanide waste with a direct binding cyanide antidote.

DETAILED DESCRIPTION

In accordance with this invention, it has been found that 2-oxopropanedioic acid is an effective cyanide antidote and an effective agent for lessening the toxicity of cyanide waste. Use of 2oxopropanedioic Acid As A Cyanide Antidote

EXAMPLE 1

Ten male ICR mice were injected intraperitoneally (i.p.) with an LD-50 dose of cyanide. Such mice were immediately thereafter given an i.p. injection of 0.2 gm/kg of 2-oxopropanedioic acid. All of the animals lived.

EXAMPLE 2

Ten male ICR mice were injected i.p. prophylactically with 0.2 gm/kg 2-oxopropanedioic acid. Such mice were then challenged with an LD-50 dose of cyanide 15 minutes later. All animals survived challenge.

EXAMPLE 3

Ten male ICR mice were injected with 0.2 gm/kg 2-oxopropanedioic acid i.p. Ten male ICR mice were injected with 2 gm/kg a-ketoglutaric acid i.p. All mice were challenged 15 minutes later with an i.p. dose of 40 mg/k g cyanide. Two out of eight animals died in each group.

EXAMPLE 4

Groups of ten male ICR mice were injected with 0.2 gm/kg 2-oxopropanedioic acid i.p. The mice were then injected i.p. with 2 gm/k g sodium thiosulfate. Fifteen minutes after the sodium thiosulfate injection an LD-50 was determined. The LD-50 of cyanide was raised from approximately 10 mg/kg to 100 mg/kg.
The Use of Direct Cyanide Bindin Agents to Reduce The Toxicity of Waste Cyanide

EXAMPLE 5

A solution of 1 mg/ml potassium cyanide was prepared. One-tenth of a milliliter of such solution per gram of body weight was injected i.p. into ten male ICR mice. Six mice died. The same solution was admixed with a 20 mg per ml of 2-oxopropanedioic acid. One-tenth of a milliliter of such admixed solution per gram of body weight was injected i.p. into ten male ICR mice. None of the mice died.

EXAMPLE 6

A solution of 1 mg/ml of potassium cyanide was prepared. One-tenth of a milliliter of such solution per gram of body weight was injected i.p. into ten male ICR mice. Five mice died. The same solution was admixed with 0.2 g per ml of a-ketoglutaric acid. One-tenth of a milliliter of such admixed solution per gram of body weight was injected i.p. into ten male ICR mice. None of the mice died.

What is claimed is:

1. A method for the treatment of cyanide poisoning comprising the administration of a therapeutically effective dose of 2-oxopropanedioic acid to a cyanide-intoxicated mammal.

2. The method of claim 1 wherein said 2-oxopropanedioic acid is admixed with a second cyanide antagonist of lower toxicity but having a lower affinity for binding cyanide.

3. A method for the prophylaxis of cyanide poisoning comprising the administration of a therapeutically effective dose of 2-oxopropanedioic acid to a mammal.

4. A method for reducing the toxicity of cyanide waste comprising admixing said cyanide waste with 2-oxopropanedioic acid.

* * * * *